United States Patent
Marras et al.

(10) Patent No.: US 11,976,037 B2
(45) Date of Patent: *May 7, 2024

(54) PROCESS FOR THE PRODUCTION OF HIGHER CARBOXYLIC ACID VINYL ESTERS

(71) Applicant: Hexion Inc., Columbus, OH (US)

(72) Inventors: Fabrizio Marras, Ottignies Louvain-la-Neuve (BE); Leo Sliedregt, Ottignies Louvain-la-Neuve (BE); Alexander Kraynov, Ottignies Louvain-la-Neuve (BE)

(73) Assignee: HEXION INC., Columbus, OH (US)

( * ) Notice: Subject to any disclaimer, the term of this patent is extended or adjusted under 35 U.S.C. 154(b) by 365 days.

This patent is subject to a terminal disclaimer.

(21) Appl. No.: 16/410,897

(22) Filed: May 13, 2019

(65) Prior Publication Data

US 2019/0330136 A1 Oct. 31, 2019

Related U.S. Application Data

(63) Continuation of application No. 15/580,487, filed as application No. PCT/EP2016/000862 on May 25, 2016, now Pat. No. 10,287,231.

(30) Foreign Application Priority Data

Jun. 8, 2015 (EP) .................................... 15075020
May 25, 2016 (WO) ................. PCT/EP2016/000862

(51) Int. Cl.
| | | |
|---|---|---|
| C07C 67/055 | (2006.01) | |
| B01J 23/44 | (2006.01) | |
| B01J 23/89 | (2006.01) | |
| B01J 31/02 | (2006.01) | |
| B01J 31/22 | (2006.01) | |
| B01J 35/00 | (2006.01) | |
| B01J 37/04 | (2006.01) | |
| C07C 67/58 | (2006.01) | |
| B01J 27/13 | (2006.01) | |
| B01J 29/072 | (2006.01) | |
| B01J 35/12 | (2006.01) | |

(52) U.S. Cl.
CPC ............. *C07C 67/055* (2013.01); *B01J 23/44* (2013.01); *B01J 23/8926* (2013.01); *B01J 31/0201* (2013.01); *B01J 31/0239* (2013.01); *B01J 31/2234* (2013.01); *B01J 31/2239* (2013.01); *B01J 35/0006* (2013.01); *B01J 37/04* (2013.01); *C07C 67/58* (2013.01); *B01J 27/13* (2013.01); *B01J 29/072* (2013.01); *B01J 35/12* (2013.01); *B01J 2231/49* (2013.01); *B01J 2531/16* (2013.01); *B01J 2531/824* (2013.01); *Y02P 20/582* (2015.11)

(58) Field of Classification Search
CPC ....... C07C 67/055; C07C 67/58; C07C 69/01; C07C 69/24; C07C 69/44; C07C 69/56; C07C 69/78; C07C 67/62; B01J 2231/49; B01J 23/44; B01J 23/8926; B01J 2531/16; B01J 2531/824; B01J 27/13; B01J 29/072; B01J 31/0201; B01J 31/0239; B01J 31/2234; B01J 31/2239; B01J 35/0006; B01J 35/12; B01J 37/04; B01J 23/72; B01J 27/122; Y02P 20/582; Y02P 20/584

See application file for complete search history.

(56) References Cited

U.S. PATENT DOCUMENTS

| | | | | |
|---|---|---|---|---|
| 3,609,180 A | * | 9/1971 | Shigematsu | ............ C07C 69/15 560/243 |
| 2003/0032831 A1 | * | 2/2003 | Yoshisato | ................ B01J 31/26 558/274 |
| 2006/0025303 A1 | * | 2/2006 | Coggan | ................ C07C 209/68 502/331 |

FOREIGN PATENT DOCUMENTS

| | | | | |
|---|---|---|---|---|
| EP | 0648734 | * | 4/1995 | |
| WO | WO-2012084644 A1 | * | 6/2012 | ............. C07C 17/08 |

* cited by examiner

*Primary Examiner* — Yevgeny Valenrod
*Assistant Examiner* — Blaine G Doletski

(57) ABSTRACT

This invention concerns a process for the production of vinyl esters of carboxylic acids with 3 to 20 carbon atoms, via vinylation in the presence of palladium (Pd) catalyst in combination with copper (Cu) as co-catalyst stabilized by organic salts in the presence of ethylene and air or oxygen.

9 Claims, 1 Drawing Sheet

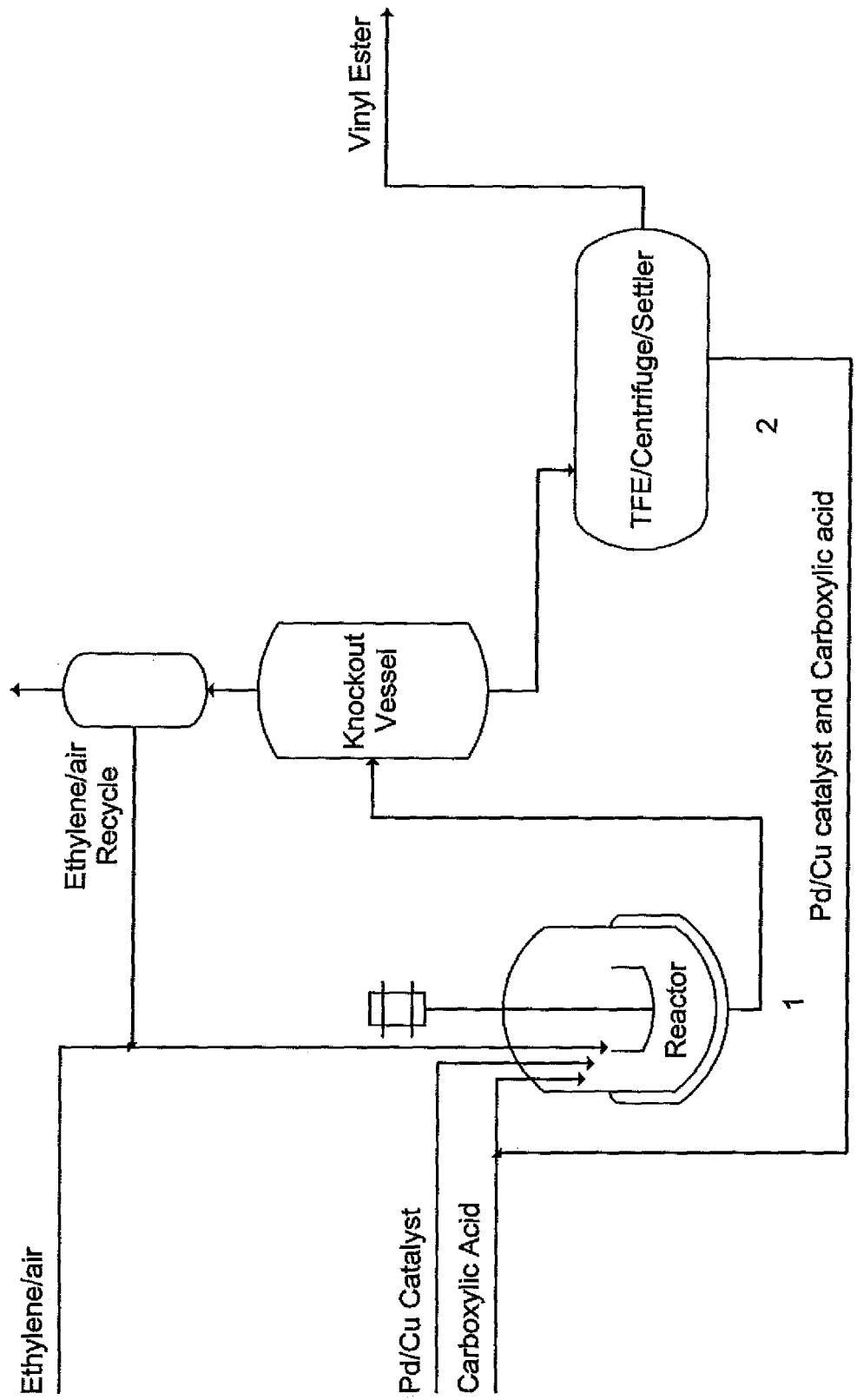

PROCESS FOR THE PRODUCTION OF HIGHER CARBOXYLIC ACID VINYL ESTERS

RELATED APPLICATION DATA

This application is a continuation application of co-pending U.S. application Ser. No. 15/580,487 with a filing date of Dec. 7, 2017, which application claims benefit to PCT Application PCT/EP2016/000862 with an International Filing Date of May 25, 2016, published as WO 2016/198147 A1, which further claims priority to European Patent Application No. EP15075020.6 filed Jun. 8, 2015, of which the entire contents of all applications are incorporated by reference herein.

TECHNICAL FIELD

This invention concerns a process for the production of vinyl esters of carboxylic acids (C3 to C20) via vinylation of carboxylic acids with ethylene in presence of palladium (Pd) catalysts in combination with copper (Cu) as co-catalyst.

BACKGROUND ART

Production of lower vinyl esters of carboxylic acid e.g. vinyl acetate from ethylene and acetic acid has been known for a long time. This reaction e.g. to vinyl acetate monomer (VAM), is carried out, usually, in gas phase using noble metal catalysts. However, such processes are not realized easily on an industrial scale when involving higher carboxylic acids. Higher boiling points of these carboxylic acids make them difficult to gasify in scalable amounts and for the same reason it is difficult to separate the vinyl esters from carboxylic acids. For these reasons, vinyl esters of higher carboxylic acids are commonly produced either by trans vinylation involving vinyl acetate and higher carboxylic acid, or by Reppe vinylation involving acetylene and higher carboxylic acid. Major drawback of transvinylation is that it needs two consecutive reactions (i) vinylation or acetoxylation step, that is the production of vinyl acetate and (ii) trans vinylation, which generates stoichiometric amount of acetic acid as side product.

Most producers of vinyl esters of higher carboxylic acids use Zn-catalyzed Reppe vinylation because the process operates by the use of a cheap Zn catalyst. However, Reppe vinylation suffers with drawbacks with respect to the raw materials as well as operational issues. Main drawback of Reppe vinylation is the use of the unsustainable reactant, acetylene as raw material. Reppe vinylation to produce vinyl esters involves high concentrations of solid catalyst, in the ranges of 30 to 70 wt %. This high concentration of solid catalyst may lead to clogging and in turn creates operational issues for the process. Further the prior art on Reppe vinylation, U.S. Pat. Nos. 6,891,052 and 1,786,647, the Zinc-catalyzed processes are known to produce acid anhydrides of carboxylic acid as by-products. However, the degree of acid anhydrides formation varies depending upon the type of carboxylic acid and the reaction conditions such as temperature. In the same art, the methods are known to convert the acid anhydride back into the carboxylic acid with the addition of water during the vinylation, although this is not without affecting the catalyst activity.

To overcome the above problems, there have been few attempts to carry out the vinylation of higher carboxylic acids in liquid phase conditions involving ethylene as raw material. They are described in U.S. Pat. No. 3,221,045 and EP0648734. U.S. Pat. No. 3,221,045 is one of the first patents to describe the vinylation process using ethylene and carboxylic acid in the presence of Pd catalyst and Cu co-catalyst system under liquid phase reaction conditions. Air or oxygen was used as terminal oxidant for the Cu-catalyst. Results demonstrated the vinylation in the absence of air while oxidizing Pd catalyst off-line in the presence of Cu co-catalyst with air or oxygen. The reported vinylation of carboxylic acids in the absence of air is of importance with respect to the process operation. However, the catalyst system displayed low catalyst activity and, in turn, this process produced low yields of vinyl esters. EP 0648734 claimed an improved process to produce vinyl esters under liquid phase reaction conditions from ethylene and higher carboxylic acids. This process used Pd(0) colloid, stabilized by a polyvinyl pyrrolidone polymer in combination with Cu as a co-catalyst and LiCl and diglyme as promoters, with the terminal oxidant being either molecular oxygen or air. This vinylation process reported low yields in the absence of solvent, while above 50% yields in the presence of solvents. These solvents include diglyme, t-amyl alcohol, t-butanol, tetrahydrofuran, and methyl propasol. The process claimed the use of Cu(II)-2-ethyl hexanoate as co-catalyst, and which resulted to increase the yields of vinyl esters. However due to the use of Cu(II)-2-ethyl hexanoate as co-catalyst the results also showed formation of considerable amounts of vinyl ester of 2-ethyl-hexanoacid as by-product along with desired vinyl ester. Additives LiCl and diglyme helped to increase the yield of vinyl ester.

In the hands of current inventors, the vinylation process with Pd(0) colloid stabilized by polyvinyl pyrrolidone polymer in the combination of Cu(II)-2-ethyl hexanoate co-catalyst was suffering from severe formation of Cu containing solid green deposits during and after reaction. Furthermore, the process was suffering from drawbacks such as (i) the use of (volatile) additives (co-solvents) during carboxylation, around 10 to 50 weight %, (ii) the difficult separation of the product from the reaction mixture because of contamination with the (volatile) additives and (iii) the limitations in concentration of Pd catalyst and Cu co-catalyst due to their limited solubility in the reaction liquid phase. In the absence of the mentioned polyvinyl pyrrolidone polymer, this process showed higher rate of vinyl ester formation, but also suffered from drawbacks such as (iv) poor stability of catalyst system, as reflected by formation of solid black-green deposits of Pd catalyst and/or Cu co-catalyst already before as well as during and after the reaction, resulting in loss of catalyst material and catalytic activity, (v) problems with the recovery of catalyst material and of catalyst activity after the reaction. In addition to the above, this patent demonstrated good yields of vinyl ester only with Cu(II)ethylhexanoate as co-catalyst precursor for different carboxylic acids. (vi) Use of Cu(II) 2-ethylhexanoate leads to concomitant formation of vinyl ester of 2-ethylhexanoic acid as by-product along with desired vinyl ester of carboxylic acid. This introduces another drawback (vii) because this mixture, containing the desired vinyl carboxylate and undesired vinyl 2-ethylhexanonate, results in a more complicated separation process of the desired vinyl ester. Further it is known art that (viii) the stabilizing agent such as polyvinyl pyrrolidone polymer is known to undergo degradation in the oxidation environments such as in vinylation reaction [Environ. Sci. Technol., 2014, 48 (22), page 13419-13426]. On a whole, the catalyst system containing Pd colloid stabilized by PVP in the combination of Cu(II)-2-ethyl hexanoate as-co-catalyst and with LiCl and polyglyame as additives employed in EP0648734 is not stable, not functional and can't afford a commercially viable process.

To solve the above problems, inventors developed a simpler and more functional catalyst system with benefits such as a long term stability, recoverability of the catalyst, and ease of product separation, while maintaining high catalyst activity and high reaction selectivity. Most importantly the newly developed Pd—Cu catalyst doesn't form inactive Pd—Cu precipitate during the reaction. The newly developed catalyst system is free of Cu salt precursors of higher carboxylic acids and hence there is no issue of co-production of undesired vinyl ester of higher carboxylic acid originating from copper salt. The new Pd—Cu catalyst system produces vinyl ester selectively, especially free of acid anhydrides of carboxylic acids during vinylation and which are commonly observed during Reppe vinylation catalysed by Zn-catalyst.

SUMMARY OF THE INVENTION

According to the current invention, the inventors designed a new Pd—Cu based catalyst system to prepare the vinyl esters from higher carboxylic acids and ethylene. The new Pd—Cu based catalytic system is prepared with organic salts acting as stabilizing and/or complexing agent. This Pd—Cu catalytic system does not need additional additives to dissolve it in reaction media. Moreover, the Pd—Cu catalytic system can act as a solvent for liquid and solid carboxylic acids at lower than reaction temperatures. Reversely, catalyst is capable to dissolve in neat liquid of carboxylic acid under reaction conditions.

After the completion of the reaction, the inventors discovered a biphasic reaction mixture where the (top) product phase contained the vinyl ester as major component and the (bottom) catalyst phase contained the catalyst complex and unreacted carboxylic acid as major components. Hence vinyl ester can be separated easily from the reaction mixture by (i) settling or (ii) centrifugation or (iii) with help of an extracting agent by liquid-liquid phase separation followed by evaporation of the product containing phase under reduced pressure or distillation or (iv) direct evaporation of product at elevated temperature under reduced pressure or (v) direct distillation of product mixture.

In the current invention, the Cu co-catalyst is free of salts of higher carboxylic acid other than the substrate of choice and hence it does not co-produce vinyl esters of higher carboxylic acids as by-product. Further the product mixture and the end vinyl ester are free of acid anhydride of carboxylic acid. This is very common by-product with the Zn-catalyzed vinylation reactions.

Another important feature of the invention is the high recovery of catalyst material and the ability to re-use the catalytic system in a next vinylation reaction with high recovery of catalytic activity. The improved long term thermal stability of the catalytic system, as supported by thermo gravimetric analysis, results in the absence of solid deposit before, during and after the vinylation reaction as well as during the steps of separation, extraction, a evaporation under reduced pressure or distillation.

BRIEF DESCRIPTION OF THE DRAWINGS

So that the manner in which the features, advantages and objects of the invention, as well as others which will become apparent, are attained, and can be understood in more detail, more particular description of the invention briefly summarized above may be had by reference to the embodiments thereof which are illustrated in the appended drawings that form a part of this specification. It is to be noted, however, that the drawings illustrate only a preferred embodiment of the invention and are therefore not to be considered limiting of its scope as the invention may admit to other equally effective embodiments.

THE FIGURE is a schematic view of a flow diagram of the vinylation reactor.

DETAILED DESCRIPTION

A process for the preparation of vinyl esters of higher carboxylic acids from higher carboxylic acids (C3 to C20) and ethylene comprises:
  Pd catalyst precursor complexed with organic salts
  Cu co-catalyst precursor is free of higher carboxylic acids anions other than of substrate carboxylic acid.
  Cu co-catalyst precursor complexed with organic salts
  Solvent-free reaction system, or optionally the use of a solvent such as (cyclic)carbonates or (cyclic) ethers
  Separation of product is achieved by phase separation followed by evaporation under reduced pressure or distillation; or by extraction with suitable extracting agent followed by evaporation under reduced pressure or distillation or direct distillation of product mixture
  Efficient re-use of the Pd—Cu catalytic system which is present in catalyst phase.
  End product, the vinyl ester of carboxylic is free of acid anhydrides of carboxylic acids.
  Key benefits of this process are summarized as follows:
  (i) Long term catalyst system stability under reaction and product separation conditions
  (ii) Tuned solubility of catalyst system in neat substrate and vice-versa, i.e. tuned solubility of substrate in catalytic system
  (iii) Solvent-free reaction system
  (iv) Ease of product separation
  (v) High recovery of the catalyst system material
  (vi) High recovery of catalyst system activity
  (vii) Ability of tailoring physicochemical properties such as stability, solubility and activity of the catalyst system by choice of cations and anions of an organic salt and metal precursor, their relative quantities and the way of preparation
  (viii) Substrate tolerance, resulting in flexibility to form vinyl esters of various carboxylic acids under similar conditions
  (ix) Free of co-production of vinyl ester of higher carboxylic acid originating from Cu(carboxylate) precursor
  (x) End product, the vinyl ester of carboxylic acid is free of carboxylic acid anhydrides

MODES OF CARRYING OUT THE INVENTION

The invention is hereafter discussed in detail. The terms palladium, Pd, Pd catalyst, Pd catalyst precursor, Pd(II) salt, supported Pd catalyst, Pd(O) colloid, Pd nanoparticles or Pd metal or Pd complex or Pd on polymer that are used in the following discussion refer to the same and mean, in the frame of this writing, precursors of the Pd catalytically active species. Similarly the copper, Cu, Cu co-catalyst, Cu co-catalyst precursor, Cu(II) or Cu(I) salt, Cu complex that are used in the following discussion are precursors of the Cu catalytically active species.

According to the invention, the inventors have found that organic salts act as complexing agent for both the Pd catalyst and Cu co-catalyst. The organic salts also act as stabilizing agent to both Pd catalyst and Cu co-catalysts and hence improving the thermal stability of Pd—Cu catalyst system under reaction and product separation conditions. Further the vinylation catalyst is re-used for several times without loss of the catalyst activity. The inventors have further found that the organic salts modify the solubility of both Pd and Cu catalysts in such a way that they are capable to mix fully with neat carboxylic acid. In particular, the Cu Co-catalyst precursor complexed by organic salts acts as solvent to dissolve the Pd catalyst precursor. This is an unique property of Cu co-catalyst developed by the current inventors compared to the prior art's catalyst system where the solubility of the Pd catalysts in carboxylic acids is one of the big problems (EP0648734).

In one embodiment of the invention, Pd precursor can form a complex by reacting with an organic salt. Similarly Cu co-catalyst precursor can form a complex by reacting with an organic salt. The organic salts to form complexes with the Pd or Cu precursors comprise of organic cations and organic/inorganic anions or combinations of organic and inorganic anions.

Organic cations can be mimics of or be based on quaternary alkyl, aryl and/or combined alkyl-aryl and/or protonated alkyl, aryl and/or mixed alkyl-aryl ammonium, phosphonium, pyridinium, pyrrolium, piperidinium, pyrrolidinium, morpholinium, imidazolium, pyrazolium and/or a mixture thereof.

Some examples of typical anions of the organic salts can be a halogen, sulfate, (halogenated)carboxylate, alkylsulfate, alkylsulfonate, trifluoromethane sulfonate, tetrafluoroborate, hexafluorophosphate, phosphate, or a mixture thereof.

The most preferred ammonium salts as complexing agent for Pd and/or Cu precursors are tetra methyl ammonium chloride, tetraethylammonium chloride, tetrabutylammonium chloride, tetrahexylammonium chloride, tetraoctylammonium chloride, cetyltrimethylammonium bromide, tetradecylammonium bromide. The most preferred phosphonium salts for complexation of Pd and/or Cu precursors are trihexyltetradecylphosphonium chloride, tetraphenylphosphonium chloride, tetramethylphosphonium iodide, and tetraphenylmethylphosphonium bromide.

In terms of Pd(II) salts that may be used as Pd catalyst precursors, many suitable Pd (II) salts are known. Pd(II) salts comprises Pd(II) cation and an anion or anions wherein the anions are selected from F—, Cl—, Br—, I—, $R_nCOO^-$, $X_m$—$R_nCOO^-$, acac-, $SO_4^{2-}$, $NO_3^{2-}$, $CN^-$, $OH^-$, $OCN^-$, $SH^-$, $R_nSO_4^-$, $NCS^-$, $R_nSO_3^-$, trifluoromethane, tetrafluoroborate, hexafluorophosphate, phosphate and combinations thereof and where $R_n$ is an alkyl, aryl, combined alkyl-aryl or cycloalkyl radical containing n=1 to 20 carbon atoms. m represents number of hydrogen atoms substituted by halogen X in $R_n$ radical, m=1 to 2n+1. Of particular interest, the anions are chloride, acetylacetonate, acetate, trifluoroacetate and hydroxide.

The Pd catalyst precursor can also from Pd metal, Pd black, or Pd deposited on a support. Many conventional supported Pd catalysts may be selected for this purpose. The preferred supports for Pd are either inorganic or organic, heterogeneous, colloidal or soluble supports. The preferred heterogeneous supports are alumina, silica, alumina and silica, natural clays, metal oxides, metal halides, molecular sieves, anionic resin, carbons and carbon oxides, their allotropes, zeolites, insoluble polymers and combinations thereof. Suitable soluble support materials for Pd are soluble polymers, dendrimers and all listed materials from the heterogeneous supports group but in colloidal state. Of particular interest are porous and nonporous $Al_2O_3$, $SiO_2$, zeolites, natural clays, molecular sieves, carbon and its allotropes, ion exchange resins, polymers or combinations thereof.

Mode of Carrying Out the Preparation of Complex of Pd Catalyst Precursor and Organic Salt According to the present invention, the Pd complex is prepared by reacting Pd precursor and organic salt. Pd complex is formed at the temperatures in range of 50 to 150° C. Most preferably the Pd complex is formed at the temperatures between 80 to 140° C. Time period of the reaction for Pd complex formation is within 2 h, and preferably less than 30 minutes. The preferred molar ratios of organic salt to Pd precursor are in the range of 4:1 to 1:1 and most preferably in the rage of 2:1 to 1:1.

The reaction of Pd catalyst precursor and organic salt is performed either in the presence of solvent or under solvent-free conditions. In the best mode of operation, the reaction of Pd catalyst precursor and organic salt is carried out without using any solvent. In other words, the Pd catalyst complex formation is also carried out in the presence of carboxylic acid substrate and in the absence of solvent. The most preferred organic solvents for the Pd catalyst formation are either (cyclic)carbonates or (cyclic)ethers. Of particular interest are propylene carbonate and diglyme.

In the best mode of operation, the Pd catalyst complex is prepared under in-situ conditions in the vinylation reaction liquid phase, prior to the start of the vinylation reaction.

Mode of Carrying Out the Preparation of Complex of Cu Precursor and Organic Salt According to the invention, a Cu co-catalyst is prepared by the reaction of Cu precursor and an organic salt. For the preparation of Cu co-catalyst, several conventional Cu salts may be used. Copper is in either Cu(I) or Cu(II) oxidation state. Most preferably Cu(II) salts are used for the preparation of Cu co-catalyst. For example, the typical anion of the metal salt can be acetylacetonate (acac), a halogen anion, $R_nCOO^-$ (n≤3), a hydroxide, carbonate, sulfate, trifluoromethanesulfonate, tetrafluoroborate, trifluoroacetate, hexafluorophosphate, phosphate, or a mixture thereof. The most preferred Cu salts comprising chloride, lower carboxylate (n<3), acetylacetonate and trifluoroacetate anions.

The reaction of Cu salt and organic salt is carried out under either ex-situ or in-situ conditions. In the best mode of operation, the Cu co-catalyst is prepared under ex-situ conditions. Inventors have found that a molar ratio range of organic salt to copper salt being 6:1 to 1:1 is optimum to prepare Cu co-catalyst. Most preferably the organic salt to copper salt molar ratios of 4:1 to 1:1 are used to prepare Cu co-catalyst.

The reaction of Cu salt and organic salt is carried out either in the presence of solvent or in the absence of solvent. Preferably the reaction of Cu salt and organic salt is carried out in the absence of solvent. Inventors have found that the Cu co-catalyst formation can also be achieved in the presence of carboxylic acid without the addition of external solvent. Preferred organic solvents for the preparation of Cu co-catalyst are (cyclic)ethers, (cyclic)carbonates or alcohols. Of particular interest the solvents for the Cu co-catalyst preparation are diglyme, propylene carbonate, (methyl)tetrahydrofuran, ethanol and (iso)propanol.

The temperature of the reaction of Cu salt and organic salt is preferably carried out in the range of 50 to 140° C. Most preferably the Cu catalyst preparation is carried out at temperatures in the range of 80 to 130° C. Reaction between Cu salt and organic salt is carried out within time of 3-5 h.

Most preferably, preparation of the Cu co-catalyst is carried out within 2 h. The reaction between Cu salt and organic salt is carried out preferably under water-free conditions, provided by inert atmosphere. Most preferably, the reaction is performed under high vacuum at elevated temperatures. Inventors also found that thus prepared Cu co-catalyst is stable and ready to use in the vinylation reaction after long storage time in a normal closed bottle at room temperature. Further, this Cu co-catalysts complexed by organic salts are capable to dissolve the Pd catalyst. The Cu co-catalysts acts as effective solvents for Pd catalyst and hence there is no requirement of additional solvents.

Vinylation of Carboxylic Acid

According to the invention, the developed catalyst and co-catalyst system is capable to vinylate various classes of carboxylic acids. The vinylation is carried out for the carboxylic acids with a total carbon atoms from 3 to 20. In particular the carboxylic acids can be of linear and cyclic alkyl, a branched alkyl, arylalkyl, alkenyl, or alkenyl-aryl. Additionally, the Pd—Cu catalyst system is capable to carry out the vinylation of carboxylic acids that are mono or multi-functional. The catalyst system can be also used for the vinylation of the carboxylic acid that contains heteroatoms in or along the carbon atom backbone and the typical heteroatoms are halogens, N, O, P, and S. Some examples of carboxylic acids with hetero atoms are trifluoroacetic acid, lactic acid, amino acids and their derivatives. Most preferable carboxylic acids for the vinylation are neodecanoic (Versatic™) acid, benzoic acid, lauric acid, 2-ethylhexanoic acid, linoleic acid, stearic acid, pivalic acid, crotonic acid, lactic acid, adipic acid, and terephthalic acid.

Vinylation of a carboxylic acid is performed with Pd catalyst wherein the Cu co-catalyst acts as oxidant together with an oxidant which acts as terminal oxidant or a sacrificial agent. Several different commonly known sacrificial oxidants can be used to oxidize Cu co-catalyst and in turn Pd catalyst. Some examples of these oxidants include oxygen, air, ozone, nitrous oxide benzoquinone, chlorine, fluorine, hypochlorite, permanganate compounds, hydro peroxide, sodium peroxide and different organic hydro peroxides. These oxidants may also be used in the absence of Cu co-catalyst to oxidize directly the Pd catalyst. Most preferably the vinylation of carboxylic acid is carried out with Pd catalyst wherein Cu co-catalyst acts as oxidant together with air or oxygen as terminal oxidant. Ethylene is used as vinylation agent for the vinylation of carboxylic acid.

Mode of Carrying Out the Vinylation Reaction

According to the current invention, the reaction medium of the vinylation of carboxylic acid is a liquid phase or a liquid phase comprising solid catalyst. Inventors found that ethylene and oxygen should be dispersed as dissolved gas phase in liquid phase in order to facilitate the vinylation reaction. For the dispersion of ethylene and oxygen or airgases in the reaction medium, several known techniques in the existing art may be used.

The vinylation process can be performed in batch, continuous or in semi-continuous process. In a batch process, certain pressures of ethylene and oxygen or air are applied to achieve the dispersion of gas phase into the reaction medium. For example a pressure of ethylene for the vinylation of carboxylic acid is applied more than 10 bar in a batch process. Further the pressure of air for the vinylation of carboxylic acid is maintained above S bar. In the best mode of operation the pressure of air is applied pressures above 10 bar. Depending upon the reaction conditions such as the catalyst and co-catalyst amounts, reactant and temperatures, the pressures of ethylene and oxygen or air may be maintained at much higher than 10 bar. Next, the vinylation of carboxylic acids is carried out at temperatures above 70° C. Depending upon the other reaction conditions, temperatures substantially higher than 70° C. may also be used. In a semi-batch reaction, gases are continuously vented and refreshed, depending upon the progress of the reaction as reflected by the consumption of air/ethylene mixture. Inventors observed this semi-continuous reaction conditions significantly increased the productivity of vinyl ester compared to simple batch process. In a continuous vinylation reaction, the concentrations of catalyst, co-catalyst, substrate and gas pressures are maintained at steady state. Most preferably the vinylation reaction is carried out in continuous mode of operation with the continuous separation of products.

In another aspect of the current invention, the vinylation of carboxylic acids is also carried out with ethylene in the absence of oxygen, while being in the presence of Pd catalyst and Cu co-catalyst. Oxidation of Cu co-catalyst and subsequently Pd catalyst is separately carried out after the vinylation reaction. Maximum vinyl ester produced in the absence of air or oxygen is not more than the Pd-catalyst and Cu co-catalyst used for the reaction and which is small. However the absence of air/oxygen substantially prevents the un-wanted side reactions from ethylene. Further, safety is another advantage of conducting vinylation in the absence of air.

According to the current invention, the inventors also found increased productivity of vinyl esters by the addition of certain additives during the vinylation. These additives include water removal agents eg. molecular sieves and chemical additives that absorb protons eg. amines. Both additives pushes chemical equilibrium towards vinyl ester. Several known water removal agents in the art may be used for this purpose. Most preferably molecular sieves 3 Å and 4 Å are preferred. Several known proton absorbing agents known in the art may be used for the purpose of absorbing protons. Of particular interest different amines can be used. Further the inventors also found that the presence of chloride anions in the reaction media have improved the yields of vinyl ester. Without bounding to any specific theory, the chloride anions affected the overall activity of catalyst positively. These chloride anions during vinylation process potentially come from Pd precursor, Cu co-catalyst precursor, organic salts, and additives.

Concentration of Pd catalyst can be used at the range of 0.001-20 mol. % with respect to the carboxylic acid, preferably below 10 mol. % and ideally below 0.1 mol. %. Cu co-catalyst can be used at the ranges of 2-400 molar equivalents with respect to Pd catalyst, preferably 4-20 equivalents (which corresponds to 0.4-2 mol. % with respect to carboxylic acid), when solubility of carboxylic acid in Pd—Cu catalytic system is not required. Amount of Cu co-catalyst can be significantly higher when solubility of carboxylic acid substrate in Pd—Cu catalytic system is required. In this case, amount of Cu co-catalyst can be at the range of 20-300 wt. % with respect to the carboxylic acid substrate, preferably 5-50 wt. %, depending on solubility of the acid substrate in specific Cu complex under typical reaction temperature.

Surprisingly the inventors have found that both the Pd and Cu complexes (prepared with organic salts) are dissolved in neat carboxylic acids e.g. Versatic acid, lauric acid, and 2-ethylhexanoic acid. Inventors have found that the Pd—Cu catalyst system produces vinyl ester of carboxylic acid at high selectivity and especially without the formation of carboxylic acid anhydrides as by-products. Carboxylic acid anhydrides are common by-products with the Zn-catalyzed Reppe vinylation reaction. The composition of the end product vinyl ester contains less than 10 ppm of acid anhydrides. Most preferably the vinyl ester of carboxylic acid produced by the Pd—Cu catalyst is essentially free of acid anhydride, down to less than 1 ppm. Further, the inventors also found that the new catalyst system is stable for longer time periods under vinylation reaction conditions. Inventors attribute the long term stability of the catalyst to new recipe of the catalyst system used. It means the catalyst system can be effectively used for the vinylation reaction with continuous introduction of raw materials required for the reaction.

According to the current invention, several known reactor materials which can withstand pressures in the range of 30-80 bar can be used for the vinylation reactor, for example stainless steel, or duplex. Most preferably the stainless steel or duplex reactors are used. Further, the dispersion of the gases in the reaction liquid phase is required for this reaction. Several known and commercially available stirring devices may be used for this purpose. Some typical examples of different dispersion systems can be from bubble columns, plate columns, packed column, trickle bed, mechanically agitated vessels, mechanical agitators such as 4-blade blade propellers, re-circulating bubble columns, surface aerators, in-line static mixers, jet ejectors, hollow axis stirrers, sparger rings buffles, plunging jets, three phase fluidized beds, and cone spinners. Under certain reaction conditions, for example at higher concentrations of catalyst and co-catalyst and at higher pressures of ethylene and oxygen, the dispersion of gases may be achieved without using specialized techniques.

The process flow diagram of the vinylation reactor can be represented as described in The FIGURE. The vinylation reaction may be performed in continuous mode using a plug flow reactor or continuous stirred-tank reactor (CSTR) type of reactor. According to the process flow diagram, the liquid phase reaction mixture after the reaction leaves the zone (1) and is transferred to a product separation unit, zone (2), where the product mixture is either settled or centrifuged followed by evaporation under reduced pressure to isolate the product. The condensed product can be further distilled to obtain higher grades, if needed. After the product separation, the reaction mixture, consisting of unreacted carboxylic acid and Pd—Cu catalytic system is pumped back into the zone 1 simultaneously with the addition of fresh carboxylic acid and gases.

Mode of the Separation of the Vinyl Ester from the Reaction Mixture

Inventors found that the vinylation reaction in the case of solvent-free conditions resulted in formation of a two phase system. The two phase are a top phase, in which vinyl ester is major component, and a bottom phase with unreacted carboxylic acid and Pd—Cu catalytic system as major components. According to the invention, the separation of the two phases is carried out by spontaneous phase separation caused by different polarity of each phase and gravitation. Further, the product vinyl ester of carboxylic acid is isolated by the evaporation of the product phase under reduced pressure or by distillation. Phase separation is performed by using several known and commercially available separation devices. Examples of some separation devices are gravity separation with inclined plates or parallel plates or corrugated parallel plates, coalesce, and hydrocyclones. Under specific reaction conditions such as longer time periods for the separation of the two phases, the isolation of vinyl ester is also carried out either by the evaporation alone under reduced pressure or direct distillation of the product reaction mixture.

In another embodiment of the invention, an extraction media is added to the reaction mixture in order to facilitate a better phase separation of the components of the reaction mixture. The preferred extraction agent should have good to excellent mutual miscibility with the desired product and low to bad miscibility with other reaction components. For this purpose, several conventional low polar solvents may be used. Of particular interest are (cyclo)pentane, (cyclo)hexane, (cyclo)heptane, petroleum ether and supercritical carbon dioxide. In this case, inventors have found that the vinyl ester extracted into the low polar phase is the major component, while the remaining phase consists of unreacted carboxylic acid together with the catalyst as major components. Further, the vinyl ester of carboxylic acid is isolated from extraction solvent by evaporation under reduced pressure. The other phase comprising of catalyst and unreacted carboxylic acid is transferred back to the reactor for the vinylation reaction.

Mode of Carrying Out the Catalyst Recovery and Re-Use

According to the invention, the inventors have found that the Pd—Cu catalytic system can be re-used for many re-cycles in a batch mode of operation or in a continuous reaction. For example in a batch reaction after the isolation of the vinyl ester, the catalyst together with the unreacted carboxylic acid are used for the next round. To continue with the next re-cycle, a certain amount of fresh carboxylic acid together with ethylene and oxygen or air may be added to the catalyst. In the case of continuous reaction, the catalyst is extracted after the accumulation of impurities and used it for the next cycle.

Representative Process Protocol

Cu co-catalyst as organometallic complex of Cu(I) or Cu(II) is prepared separately by mixing the Cu co-catalyst precursor and organic salt (in the presence of a solvent if needed) for several hours at 100-120° C. followed by vacuum drying. If present, solvent is removed by evaporation under reduced pressure, and resulting material is stored at room temperature in closed bottle.

For each experiment, the required amounts of Pd precursor and organic salt (alternatively, separately prepared Pd catalyst complex) and Cu complex described above are taken up in neat carboxylic acid substrate.

The resulting mixture is heated to 80-130° C. while stirring.

Once the required temperature is attained, stirring is paused for short time, the reaction is started by administration of 30 bar ethylene, followed by administration of air up to a total pressure of 50 bars and restarting of stirring. The gas venting refreshing procedure is applied during the progress of reaction as reflected by gas consumption (pressure drop).

To terminate the reaction, the mixture is allowed to attain ambient temperature, reaction gases are released.

The vinyl ester of a carboxylic acid of interest is isolated from the reaction mixture by one of the methods described above.

If desired, the catalyst phase residue is used for a next reaction cycle without further processing. A fresh amount of carboxylic acid substrate may be added.

EXAMPLES

Comparative Example 1, Use of Pd(0)/PVP as Pd Precursor

Preparation of Pd(O)/PVP stock solution: A round bottom flask was charged with 0.69 g $Na_2PdCl_4$, 0.88 g polyvinylpyrrolidone (PVP-K15) and 385 mL methanol. The resultant solution is refluxed for 30 minutes. To this 16 mL of a 0.5 M NaOH solution in methanol was added and refluxed for an additional 20 minutes. The solution turns dark brown when Pd(0) is being formed. The reaction mixture is cooled down to room temperature and the solution is stored in a suitable storage vessel under nitrogen after emptying the reactor.

For vinylation reaction, $1/10^{th}$ of the above stock solution is used. Methanol is evaporated from this $1/10^{th}$ part of the stock solution. The resultant Pd(0) colloid stabilized on PVP-K15 is re dispersed in an appropriate amount of organic medium, that is versatic acid and solvent of the vinylation reaction.

Vinylation Reaction of Neodecanoic Acid:

26.5 g of Cu(II)(neodecanoate) used in the vinylation reaction and which is obtained by the evaporation of toluene from the commercially available Cu(II)(neodecanoate) in toluene solution. Initially the reactor is filled with Pd(0)/PVP15 dispersed in neodecanoic acid and 72.8 g of diglyme followed by Cu(neodecanoate) dispersed in neodecanoic acid, and 0.5 g of LiCl dispersed in 8.9 g of N-methylpyrrolidine (NMP). Total 35.5 g of neodecanoic acid was used for the vinylation reaction. Stirring of the reactor is set at 1000 rpm and flushed the reactor three times with nitrogen. Temperature of the reactor is set at 110° C. and the stirring is continued at 1000 rpm. Reactor is pressurized with 20 bar of ethylene followed by air to increase the pressure to 35 bar. Samples are collected for the analysis at regular intervals. Monitor of pressure drop also helped the cease of the vinylation reaction.

Results

During the vinylation reaction and at the end of the reaction, formation of green precipitate is observed. This green precipitate is identified as Pd and Cu precipitate in ICP studies. Further the green precipitate is found to be inactive for vinylation reaction. GC analysis of the sample taken at the end of the reaction showed 77% yield of VeoVa.

Comparative Example 2, Use of $Na_2PdCl_4$ as Pd Precursor

Vinylation Reaction of Neodecanoic Acid:

Pd(0)/PVP15 is replaced by $Na_2PdCl_4$ as Pd precursor in this vinylation reaction. Ingredients of the vinylation reaction are prepared as follows: 0.07 g of $Na_2PdCl_4$ was dissolved in 72.8 g of diglyme. 3.82 g of Cu (II)(neodecanoate) was dissolved in 36.7 g of Neodecanoic acid. Similarly 0.5 g of LiCl is dissolved in 8.9 of NMP. All the solutions were stirred and if necessary warmed until solid material had disappeared. The Cu(neodecanoate) solution was added to the Pd (II) solution. This mixture was added to LiCl solution. The resultant mixture was used immediately as a stock solution for the next steps. Temperature of the reactor is set at 110° C. and the reaction mixture stirred at 1000 rpm. Reactor was left to slowly attain its set temperature under atmospheric pressure. Vinylation reaction was started by pressurizing the reactor with ethylene 20 bar. Immediately after that the same reactor was further pressurized with air up to 35 bar. It should be noted that the gas phase in the reactor was vented and refreshed during the experiment when the pressure drops below 10 bar. After the final sample, the end total pressure was determined and the reaction mixture was cooled to ambient temperature. The gas phase in the reactor was vented and refreshed with nitrogen.

Results

GC analysis of the sample taken at the end of the reaction showed 76% yield of VeoVa. By the end of the reaction, uncontrolled formation of Pd black is observed. This results in loss of catalyst material.

Comparative Example 3, Use of $Cu(OH)_2$ as Cu Co-Catalyst

Vinylation Reaction of Neodecanoic Acid:

In this reaction, the Cu precursor Cu(neodecanoate) is replaced by $Cu(OH)_2$. 0.07 g of $Na_2PdCl_4$ was dissolved in 72.8 g of diglyme. 0.91 g of Cu(OH)2 was dissolved in 35.5 of Neodecanoic acid. Similarly 0.5 g of LiCl is dissolved in 8.9 of NMP. All the solutions were stirred and if necessary warmed until solid material had disappeared. The Cu(neodecanoate) solution was added to the Pd (II) solution. This mixture was added to LiCl solution. The resultant mixture was used immediately as a stock solution for the next steps. Temperature of the reactor is set at 110° C. and the reaction mixture was stirred at 1000 rpm. Reactor was left to slowly attain its set temperature under atmospheric pressure. Vinylation reaction was started by pressurizing the reactor with ethylene 20 bar. Immediately after that the same reactor was further pressurized with air up to 35 bar. It should be noted that the gas phase in the reactor was vented and refreshed during the experiment when the pressure drops 5 bar than the initial set pressure or at regular intervals of 30 minutes. After the final sample, the end total pressure was determined and the reaction mixture was cooled to ambient temperature. The gas phase in the reactor was vented and refreshed with nitrogen.

Results

By the end of the reaction, undesired formation of Pd black is observed. GC analysis of the sample taken at the end of the reaction showed 79% yield of VeoVa.

Comparative 4, Use of Propylene Carbonate as Solvent and Pd(Acac)2 as Pd Precursor Preparation of the Reaction Liquid Phase 1.72 g (10 mmol) of Versatic acid (VA 10) was dissolved in 72 g of propylene carbonate in a glass vessel at room temperature. Homogeneous solution was obtained after good shaking. Next, 39 mg (0.4 mmol) of $Cu(OH)_2$ were introduced into thus obtained solution. The reaction vessel was transferred to a preheated (70° C.) oil bath and the mixture was stirred for ca. 2 hours. After that, 30 mg (0.1 mmol) of $Pd(acac)_2$ were added and stirring was continued for another 15 min, resulting in complete dissolution of Pd precursor. Separately, a LiCl solution was prepared in NMP by adding 17 mg (0.4 mmol) of LiCl to 4.4 g (44.8 mmol) of NMP. This Li salt solution was added to the Pd/Cu containing solution. The resulting mixture was transferred to a metal autoclave reactor.

Performing Reaction

To start the reaction, the metal reactor containing the reaction mixture was preheated at 90° C. A pressure of 30 bar of ethylene was introduced into the reactor, followed by introduction of air to a total pressure of ca. 50 bar. After that, stirring was started. After two hours, the reactor was cooled to ca. 25-30° C. and gas pressure was released. The reactor was purged with nitrogen and then opened. The reaction mixture was collected and stored for analysis.

Results

GC analysis of a sample taken from the reaction liquid phase after 2 hours showed concentration of VeoVa 10 to be 0.5 wt. %, that corresponds to 20% of the yield. Use of propylene carbonate as solvent helped to minimize the formation of undesired Pd black.

Comparative 5, in the Absence of NMP and LiCl

Preparation of the Reaction Liquid Phase

First, 1.72 g (10 mmol) of VA 10 was dissolved in 72 g of propylene carbonate in a glass vessel at room temperature. Homogeneous solution was obtained after good shaking. Then, 39 mg (0.4 mmol) of $Cu(OH)_2$ were introduced into thus obtained solution. The reaction vessel was transferred to a preheated (70° C.) oil bath and the mixture was stirred for ca. 2 hours. After that, 30 mg (0.1 mmol) of $Pd(acac)_2$ were added and stirring was continued for another 15 min, resulting in complete dissolution of Pd precursor. No LiCl was added.

Vinylation reaction is performed similar to the comparative example 4.

Results

GC analysis of sample taken from the reaction liquid phase after 2 hours showed concentration of VeoVa 10 to be ≤0.1 wt. % (close to detection limit) that corresponds to formal yield≤4%.

case of EP0648734, the use of Cu(II)2-ethyl hexanoate always results to produce stoichiometric amounts of vinyl 2-ethylhexanoate as by-product along with the desired vinyl ester. Further simple Pd(II) salt is found be comparable active as Pd(0)/PVP colloid, the later needs additional preparation methods (comparative example 2). However, in comparative examples 2 and 3 formation of undesired Pd black at the end of vinylation reaction was observed. Current inventors also found simple Cu(II) salt serve the same purpose as Cu(II) 2-ethylhexanoate (comparative example 3). Cu(II) 2-ethylhexanoate is an expensive reagent or requires additional synthesis steps. The results from the prior art displayed high yield of vinyl ester of neodecanoic acid only in the case of Cu(II)2-ethylhexanoate used as Cu precursor (EP0648734). Current inventors found in the absence of NMP and LiCl as additives, the yield of vinyl ester is below the detection level of the GC method (comparative 4 and 5).

In the tables 2 and 3 below we summarize results of the performed experiments supporting the current invention.

TABLE 1

Vinylation of neodecanoic acid (Versatic acid) in presence of Pd based catalyst and Cu based co-catalyst and ethylene (comparative examples).

| Example | Temp., ° C. | Cu precursor | Pd cat. or precursor | Additive | Reaction solvent | Time, h | Vinyl ester Yield, % |
|---|---|---|---|---|---|---|---|
| EP0648734, example 25[1]) | 110 | Cu(II) 2-ethylhexanoate | Pd(0) colloid in PVP | LiCl NMP | Methyl propasol | 2 | 37 |
| 1 | | $Cu(neodecanoate)_2$ | Pd(0) colloid in PVP | NMP LiCl | Diglyme | 4.5 | 77 |
| 2 | | $Cu(neodecanoate)_2$ | $Na_2PdCl_4$ | NMP LiCl | Diglyme | 4.5 | 76 |
| 3 | | Cu(OH)2 | Na2PdCl4 | NMP LiCl | Diglyme | 2.1 | 79 |
| 4 | 90 | $Cu(OH)_2$ | $Pd(II)(acac)_2$ | LiCl NMP | Propylene carbonate | 2 | 20 |
| 5 | 90 | $Cu(OH)_2$ | $Pd(II)(acac)_2$ | No | Propylene carbonate | 4 | <4 |

[1]This example contains the best results obtained for synthesis of vinyl neodecanoate in EP0648734; Calculated TONs for vinyl decanoate = 354; An un quantified amount of Vinyl 2-ethyl hexanoate was produced.

Discussion:

Table 1 presents the comparative examples of vinylation of neodecanoic acid. The closest prior art, EP0648734 claimed the use of Pd(O) colloid as Pd catalyst, and Cu(II) 2-ethyl hexanoate as co-oxidant for vinylation reaction. The prior art also claimed the use of polyglyme as an additive while LiCl and NMP are also being used as additives for the vinylation reaction. Current inventors have discovered the complex or cumbersome recipe of catalyst system as proposed in prior art is not necessary for the vinylation. Comparative example 1 is resulted to produce green precipitate at the end of the reaction. Formation of Cu containing green precipitate results in undesired loss of Cu Co-catalyst material. It is found that the Cu(II) oxidant, the Cu(II) neodecanoate is equal or better than Cu(II) 2-ethyl hexanoate (comparative example 1) as Cu precursor. In the

TABLE 2

Vinylation of neodecanoic acid (Versatic acid) in presence of ethylene and air over new Pd—Cu catalytic system, (examples of invention) performed at 100° C.

| Example | Acid, mmol | Precursors for Cu co-catalyst | Precursors for Pd catalyst | solvent | Time, h | TON (for Vinyl ester) | Yield (%) |
|---|---|---|---|---|---|---|---|
| 1 | 123 | $Cu(oAc)_2$ $Bu_4NCl$ | $Pd(acac)_2$ $Hex_4NCl$ | No | 12 | 1074 | 87 |
| 2 | 349 | $CuCl_2$ $P_{66614}Cl$ | $Pd/Al_2O_3$ $Hex_4NCl$ | No | 13 | 133 | 46 |
| 3* | 100 | $Cu(OAc)_2*H_2O$ $Hex_4NCl$ | $Pd(acac)_2$ $Hex_4NCl$ | PC | 6 | 410 | 43 |
| 4 | 100 | $Cu(OAc)_2$ $Bu_4NCl$ | $Pd(acac)_2$ $Hex_4NCl$ | PC | 7 | 820 | 82 |

TABLE 2-continued

Vinylation of neodecanoic acid (Versatic acid) in presence of ethylene and air over new Pd—Cu catalytic system, (examples of invention) performed at 100° C.

| Example | Acid, mmol | Precursors for Cu co-catalyst | Precursors for Pd catalyst | solvent | Time, h | TON (for Vinyl ester) | Yield (%) |
|---|---|---|---|---|---|---|---|
| 5 | 123 | Cu(OAc)$_2$ Bu$_4$NCl | Pd(acac)$_2$ Hex$_4$NCl | No | 13 | 499 | 81 |
| 6a | 100 | Cu(acac)$_2$ Hex$_4$NCl | Pd(acac)$_2$ Hex$_4$NCl | PC | 5 | 672 | 67 |
| 6b | 60** | Cu(acac)$_2$ Hex$_4$NCl | Pd(acac)$_2$ Hex$_4$NCl | PC | 5 | 490 | 41 |
| 6c | 61** | Cu(acac)$_2$ Hex$_4$NCl | Pd(acac)$_2$ Hex$_4$NCl | PC | 5 | 534 | 22 |
| 7 | 348 | CuCl$_2$ P$_{66614}$Cl | Pd/Al$_2$O$_3$ No | No | 6 | 70 | 19.5 |
| 8 | 348 | Cu(CF$_3$COO)$_2$ P$_{66614}$Cl | Pd/Al$_2$O$_3$ No | No | 4 | 45 | 12 |
| 9 | 169 | Cu(I)Cl Bu$_4$NCl | Pd(acac)$_2$ Hex$_4$NCl | No | 5 | 424 | 20 | acac: acetylacetonate
OAc: acetate
PC: propylene carbonate
Yield =100% * (mmol of formed Vinyl ester)/(mmol of carboxyli acid taken initially)
*Spontaneous liquid-liquid phase separation between product phase and catalyst phase was found. We also demonstrate an improvement of phase separation phenomena (after reaction) by adding non-polar hexane. The improvement comprises
Significantly less time needed for phase separation to happen (compared to when no hexane was used)
Phase separation is clear and sharp
Metal loss of Cu and Pd is lower when hexane was used.
**Values were estimated based on sum of VA10 remaining after each separation cycle and freshly added quantities.
**50% loss of Pd is observed for Pd/Cu catalyst in each round due to handling. TONs are calculated based on the reduced amount of Pd.

Example 1, Use of Ammonium Salt

Preparation of Cu Co-Catalyst 24. g (86.5 mmol) of tetrabutylammmonium chloride were dissolved in ca. 200 ml THF at 55-60° C. under continuous stirring. 7.8 g (43.2 mmol) of anhydrous Cu(II) acetate dissolved in preheated THF was slowly added to the tetrabutylammmonium chloride containing solution that resulted in color turning from blue to green. After 30 min of stirring at ca. 65° C., THF was removed with help of a rotary evaporator.

Preparation of the Reaction Liquid Phase 36 mg (0.12 mmol) of Pd(acac)$_2$ together with 126 mg (0.32 mmol) of tetrahexylammonium chloride were dissolved in 21.3 g (123.5 mmol) of VA 10 at 80° C. Cu co-catalyst of 3 g of prepared as described above were added into Pd containing VA 10 solution. The reaction mixture was transferred to a high pressure reactor.

Performing Reaction:

To start the reaction, the reactor containing the corresponding reaction mixture was preheated and stirred at 100° C. After the desired temperature had been attained, stirring was stopped and a pressure of 30 bar of ethylene was introduced into the reactor, followed by introduction of air to a total pressure of ca. 50 bar. After that, stirring was restarted. Gas consumption was monitored with help of a pressure indicator. When the gas consumption was approaching zero, stirring was stopped, the remaining gas was slowly released and the reactor was recharged with 30 bar of ethylene, followed by introduction of air to a total pressure of 50 bar. After that, stirring was restarted. The venting-refreshing procedure was applied as many times as needed during the experiment. Finally, the reactor was purged with nitrogen and then opened. The reaction liquid phase was collected and stored for GC analysis.

The GC analysis of sample taken from the reaction mixture after 12 hours showed concentration of VeoVa 10 and versatic acid to be 79.7 wt. % and 10.2 wt. %, which corresponds to apparent TON$_{pd}$=1075 and yield of 87%.

Example 2, Use of Pd/Al$_2$O$_3$ as Pd Precursor (According to Invention)

Preparation of Cu Co-Catalyst

First, 30 g (178.4 mmol) CuCl$_2$ and 92.7 g (178.4 mmol) trihexyltetradecylphosphonium chloride were mixed together at 80° C. under nitrogen followed by vacuum. Temperature was gradually increased to 120° C. and maintained for next 3 hours.

Preparation of the Reaction Liquid Phase

First, 3.34 g of the Cu co-catalyst mentioned above was added to a mixture of 60.0 g (348.5 mmol) of VA 10 and 6.2 g of tetradecane (internal standard) at 80° C. under constant stirring. The resulting visually homogeneous solution was transferred to a high pressure reactor. To the mixture, 1.3 g of heterogeneous Pd/Al$_2$O$_3$ (10% Pd) commercial catalyst and 974 mg (2.5 mmol) tetrahexylammonium chloride were added.

Vinylation reaction was carried out similar to the example 1.

Results

After 13 hours under said reaction conditions, a sample of the reaction liquid phase was analyzed by gas chromatography to determine the composition. The reaction mixture was found to contain 162.3 mmol vinyl ester of neodecanoic acid (VeoVa) that corresponds to formal yield of 46.5% and TON=125.

Example 3, Use of Propylene Carbonate as Solvent (According to Invention)

Preparation of the Reaction Liquid Phase

In order to prepare propylene carbonate solution of Cu co-catalyst, 80 mg (0.4 mmol) of Cu(OAc)$_2$*H$_2$O were added to a solution of tetrahexylammonium chloride (312 mg or 0.8 mmol) in 24 g of propylene carbonate at 60° C. under constant stirring. The Pd containing solution was prepared via addition of 30 mg (0.1 mmol) of Pd(acac)$_2$ to a solution of tetrahexylammonium chloride (78 mg or 0.2 mmol) in 48 g of propylene carbonate at 60° C. under constant stirring. Both the Cu and Pd solutions were transferred into high pressure reactor and VA 10 (17.23 g or 100 mmol) were added.

Vinylation reaction is carried out similar to example 1

Results

After the reaction, the reaction mixture was found to be biphasic at room temperature. Both bottom and top phases were analyzed separately. GC analysis of the bottom phase showed concentration of VeoVa and VA10 to be 39 wt. % and 8.0 wt. %. GC analysis of the top phase showed concentration of VeoVa and VA10 to be 23% wt. and 72.4 wt. %. Formal TON=430 and yield=41% were found.

Example 4, Use of Propylene Carbonate as Solvent

Preparation of Cu Co-Catalyst:

The Cu co-catalyst was prepared by slow addition of 100 ml of THF solution of anhydrous Cu(OAc)$_2$ (7.85 g or 43.25 mmol) in to a solution of 24.0 g (86.5 mmol) of tetrabutylammonium chloride in 200 mL of THF at 60° C. under constant stirring. After few minutes, the reaction mixture became visibly homogeneous and after 15 min the solvent THF was removed under vacuum and elevated temperature.

Preparation of the Reaction Liquid Phase

A solution of Pd(acac)$_2$ (30 mg, 0.1 mmol) and tetrahexylanmonium chloride (78 mg, 0.2 mol) in 10 g of propylene carbonate was added to 44 g of propylene carbonate containing 11.1 g of the above described Cu complex. Finally, 17.2 g (100 mmol) of VA 10 were added and the mixture was transferred to a high pressure reactor.

Vinylation reaction was conducted for 7 h similar to the example 1.

Results

GC analysis of sample taken from the reaction mixture after 7 hours showed concentration of VeoVa and VA10 to be 18.8 wt. % and 2.7 wt. %. Formal TON of 820 and Yield=82% were found.

Example 5, Demonstration of the Phase Separation of the Reaction Mixture Under Solvent Less Conditions Preparation of the Reaction Liquid Phase First, Pd(acac)$_2$ (66 mg, 0.2 mmol) and tetrahexylammonium chloride (156 mg, 0.4 mol) were added to 21.23 g (123 mmol) of VA 10. The mixture was heated at 80° C. under constant stirring for 1 hour. Next, 2.95 g of the Cu complex described in Example 4 were added to this mixture and after another 15 min of stirring, the reaction mixture was transferred to a high pressure reactor.

Vinylation reaction was conducted for 13 h similar to the example 1.

Results

Surprisingly, a biphasic reaction mixture was obtained after 13 h of reaction time. Analysis of the larger top phase (ca. 19 g) revealed the concentration of VeoVa and VA10 to be 72 wt. % and 14.9 wt. %, respectively. ICP analysis of this phase showed presence of 5.1% of Pd and 5.3% of Cu with respect to their initial quantities used in preparation of the reaction liquid phase. Formal TON of 499 and yield of 81% were achieved.

When hexane (30 g) and the mentioned top phase (14 g) were mixed together and shaken, again phase separation was observed. Analysis of the top phase thus obtained revealed the concentration of VeoVa10 and VA10 to be 69.2 wt. % and 16.8 wt. %. ICP analysis of the same top phase showed presence of 2.3% of Pd and 0.2% of Cu with respect to their initial quantities used in preparation of the reaction liquid phase.

Example 6, Demonstration of the Re-Use of the Catalyst

6.A First Round

Preparation of the Reaction Liquid Phase

First, 1.3 g (5.1 mmol) Cu(acac)$_2$ and 3.9 g (9.9 mmol) tetrahexylammonium chloride were taken up in 20.0 mL propylene carbonate at 100° C. under constant stirring. Similarly, 0.064 g (0.21 mmol) Pd(acac)$_2$ and 0.16 g (0.38 mmol) tetrahexylammonium chloride were taken up in 91.8 g propylene carbonate at 50° C. under constant stirring. Once both solutions were visually homogeneous, 16.0 mL of the Cu solution and 45.7 g of the Pd solution were combined and transferred to a high pressure reactor. 17.3 g (100 mmol) of VA 10 were added to this mixture.

First round of vinylation was conducted similar to typical reaction method described in the above examples.

Results

Samples of the reaction liquid phase, collected after 5 and 15 hours under said reaction conditions, were analyzed by gas chromatography to determine the composition. The sample collected after 5 h contained 15.3 wt. % of the product VeoVa10. The sample collected after 15 h contained 16.3 wt. % of the product VeoVa10. The reaction mixture was collected after 15 h reaction time, and was mixed with 40 mL hexane. The two phases were separated, resulting in 34.6 g bottom (reaction) phase and 32.1 g top (hexane) phase. According to GC analysis, the bottom phase contained 1.63 wt. % VeoVa10, while the top phase contained 18.38 wt. % VeoVa10. The bottom phase was used for the next round. Reaction rate as a linear approximation between zero time and 5 h, was estimated to be 134 l/h. Pd/Cu catalyst recovered as bottom phase after extraction has lost approximately 50% of Pd in the first round compared to the initial Pd at the start. Loss of Pd is mainly due to the handling of phases and the corresponding transfer.

6.B Second Round:

Preparation of Liquid Phase:

First, 32.9 g of the bottom phase from extraction after the first round were transferred into a high pressure reactor. To this mixture, 9.9 g (58 mmol) of VA 10 were added. A sample of the reaction liquid phase was analyzed by gas chromatography to determine the composition. The mixture contained 1.4 wt. % of the product VeoVa 10, remaining after the first round.

Second round of vinylation was carried out for 11 h in typical method as described in the above examples. TONs for vinyl ester are calculated based on the reduced Pd amount in the second round. Like in first round, an estimated 50% of Pd loss is also observed in the second round.

Results

Samples of the reaction liquid phase, collected after 5 and after 11 hours under said reaction conditions, were analyzed by gas chromatography to determine the composition. The sample collected after 5 h contained 12.53 wt % of the product VeoVa10. The sample collected after 11 hours contained 17.81 wt % of the product VeoVa10.

The reaction mixture, obtained after 11 hours, was mixed with 30 mL hexane. The two phases were separated, resulting in 22.16 g bottom (reaction) phase and 24.07 g top (hexane) phase. According to GC analysis, the bottom phase contained 1.89 wt. % VeoVa10, while the top phase contained 19.05 wt. % VeoVa10. The bottom phase was used for the next round. The apparent reaction rate after 5 hours was estimated to be 98 l/h. TONs for vinyl ester are calculated based on the reduced Pd amount in the second round.

6.C Third Round:

Preparation of Liquid Phase

First, 20.07 g of the bottom phase from extraction after the second round were transferred into a high pressure reactor. To this mixture, 10.07 g (58 mmol) of VA 10 was added. A sample of the reaction liquid phase was analyzed by gas chromatography to determine the composition. The mixture contained 2.8 wt. % of the product VeoVa10.

Vinylation reaction in the third round was carried out for 5 h similar to typical method used in the above examples.

Results

After 5 hours under said reaction conditions, a sample of the reaction liquid phase was analyzed by gas chromatography to determine the composition. The mixture contained 10.99 wt. % of the product VeoVa10. The apparent reaction rate after 5 hours was estimated to be 107 l/h.

Based on the observed relatively constant values of the reaction rate (98-134 l/h) within the first three rounds, we conclude that the Pd—Cu catalytic system under these conditions show no or only minor loss of catalytic activity in the vinylation process.

Example 7 Use of Supported Pd Catalyst without Additive

Preparation of the Reaction Liquid Phase 6.35 g of tetradecane as internal standard, 1.02 g (0.96 mmol Pd) of commercial Pd catalyst supported on alumina and 1.32 g Cu co-catalyst described in example 2 were added to 60.02 g (348 mmol) of VA 10 at room temperature being already in high pressure reactor. No tetrahexylammonium chloride was added.

Vinylation was carried out for 7 similar to typical method described in the above examples Results GC analysis of sample taken from the reaction mixture after 6 hours showed presence of 66.7 mmol of VeoVa 10 and 269 mmol VA 10 in the reactor that corresponds to formal yield of 19.5% and TON=71.

Example 8, Use of Cu(II) Trifluoroacetate Hydrate as Copper Precursor

Preparation of Cu Co-Catalyst 15 ml of ethanolic solution of Cu(II) trifluoroacetate hydrate (3.64 g) was added to 10 ml of ethanolic solution of trihexyltetradecylphosphonium chloride (5.98 g, 11.53 mmol) at room temperature and under continuous stirring. After ca. 30 min of stirring, ethanol was removed and the resulting material was dried under high vacuum at 120° C. for 2 hours.

Preparation of the Reaction Liquid Phase 6.03 g of tetradecane, 4.69 g of Cu co-catalyst (prepared as described here) and 1.01 g of Pd/Al$_2$O$_3$ catalyst (0.95 mmol Pd) were added to 60.0 g (348.3 mmol) of VA 10 being in high pressure reactor.

Vinylation reaction was carried out similar to the typical method used in the above examples.

Results

GC analysis of the sample taken after 30 min of reaction time showed 20.5 mmol of VeoVa and 328.7 mmol VA10 present in the reactor that corresponds to formal yield=6%, TON=22 and TOF=43 l/h. Sample taken after 4 hours of reaction time showed 46.3 mmol of VeoVa that corresponds to 13% yield and TON=49.

Example 9, Use of Cu(I)Cl as Cu Co-Catalyst Precursor

Preparation of Cu Co-Catalyst

First, 1507 mg (15.22 mmol) Copper (I) chloride taken as solid powder was manually mixed with solid tetrabutylammonium chloride (4.23 g, 15.22 mmol) in a glass flask. Then the flask was equipped with a magnetic stirrer, filled with nitrogen gas and moved into oil bath (preheated to 90° C.) for 1 h. Next, temperature was set to 120° C. for next 5 hours.

Preparation of the Reaction Liquid Phase:

Pd containing solution was prepared in a closed 100 mL vessel on a stirring/heating plate at 50-70° C. Thus, 30.5 g (0.1 mmol) of Pd(acac)$_2$ were dissolved completely in 17.72 g of VA 10, and then tetrahexylammonium chloride (80 mg, 0.2 mmol) was added. The stirring was continued for 1-2 hrs. Cu containing solution was prepared by dissolving 155 mg of Cu(I) co-catalyst, described in this example, in 16.64 g of VA 10 at 70° C. Finally, both solutions were mixed in high pressure reactor. In total 34.36 g (200 mmol) VA 10 was used.

Vinylation was carried out for in a typical method used in the above examples.

Results

GC analysis of the sample taken after 5 h showed 21 wt. % of concentration of VeoVa in the reaction mixture that corresponds to formal yield of 16 or 20%.

In the experiments below we describe vinylation of some other carboxylic acids.

Discussion

Table 2 examples of current invention produced yields as high as above 80% and TONs above 1000 in single cycle for vinyl neodecanoate under solvent-free conditions. Use of solvent, propylene carbonate also produced yields above 80% and TONs above 800 TONs for vinyl neodecanoate. Compared to the current invention, a maximum yield of 37% and TONs of 350 for vinyl neodecanoate using an organic solvent, methyl propasol is reported in the closest prior art, EP0648734. Experiment 6 of current invention demonstrated the re-use of catalyst for 3 cycles and produced cumulative TON of above 1500 for vinyl neodecanoate. This is only a representative experiment and the catalyst is capable to achieve bigger TONs for vinyl ester. These results clearly indicate that the vinylation process of current invention is far better with respect to the increased yields and TONs of Vinyl neodecanoate.

In the same prior art, EP0648734 a maximum yield of 19% for any vinyl ester, Vinyl 2-ethyl hexanoate under solvent-free conditions is reported while a maximum yield of 69% is reported using an organic solvent.

TABLE 3

Vinylation of some other carboxylic acids in presence of ethylene and air over Pd—Cu catalytic system[1] and (examples of invention).

| Example | Name of acid (quantity) | Pd cat. | Reaction solvent | Time, h | TONs (of Vinyl ester) | Yield (%) |
|---|---|---|---|---|---|---|
| 10 | Lauric acid (349 mmol) | Pd(oAc)$_2$ Hex$_4$NCl | No | 6 | 80 | 16 |
| 11 | 2-ethyl hexanoic acid (462 mmol) | Pd(oAc)$_2$ Hex$_4$NCl | no | 7 | 60 | 17 |
| 12 | Benzoic acid (248 mmol) | Pd(acac)$_2$ Hex$_4$NCl | Diglyme | 7 | 125 | 45 |
| 13 | Pivalic acid (453 mmol) | Pd(oAc)$_2$ Hex$_4$NCl | None | 8 | 100 | 22 |
| 14 | Adipic acid (169 mmol) | Pd black/ Hex$_4$NCl | 1,4-dioxane | 21 | 27 | 16 |
| 15 | Crotonic acid 661 mmol | Pd black/ Hex$_4$NCl | None | 4 | 54 | 8 |

[1]The same Cu co-catalyst prepared from CuCl$_2$ and P$_{66614}$Cl was used as in example 2, in example 13, Cu co-catalyst was prepared from CuCl$_2$ and N$_{6666}$Cl.

Example 10, Vinylation of Lauric Acid

Preparation of the Reaction Liquid Phase

First, 392 mg (1.75 mmol) of Pd(OAc)$_2$ together with 1.36 g (3.49 mmol) of tetrahexylammonium chloride and 6.79 g of the Cu co-catalyst described in example 2 were added to a high pressure reactor containing 70 g (349.44 mmol) of lauric acid. Stirring was started once temperature was high enough to melt the mixture.

Reaction was carried out in typical way described in the above examples.

Results

After 6 hours under said reaction conditions, a sample of the reaction liquid phase was analyzed by gas chromatography to determine the composition. The mixture contained 15 wt. % of the product vinyl laurate.

Example 11, Vinylation of 2-Ethylhexanoic Acid

Preparation of the Reaction Liquid Phase 347 mg (1.55 mmol) of Pd(oAc)$_2$ together with 0.66 g (1.7 mmol) of tetrahexylammonium chloride and 2.18 g of the Cu co-catalyst described in example 2 were added to a high pressure reactor containing 66.64 g (462 mmol) of 2-ethylhexanoic acid (EHA).

Vinylation reaction was carried out in typical way in the above examples.

Results

After 7 hours under said reaction conditions, a sample of the reaction liquid phase was analyzed by gas chromatography to determine the composition. The mixture contained 16 wt. % of the product vinyl 2-ethylhexanoate (VEHA).

Example 12, Vinylation of Benzoic Acid

Preparation of the Reaction Liquid Phase

Because of high melting point of benzoic acid, a minimal amount of diglyme was use to liquefy it at reaction temperature. 303 mg (0.995 mmol) of Pd(acac)$_2$ together with 0.818 g (2.1 mmol) of tetrahexylammonium chloride and 5.3 g of the Cu co-catalyst described in example 2 were added to a high pressure reactor containing 30.33 g (248.4 mmol) of benzoic acid with 15.8 g of diglyme.

The vinylation reaction was carried out typical way described in the above examples.

Results

After 7 hours under said reaction conditions, a sample of the reaction liquid phase was analyzed by gas chromatography to determine the composition. The mixture contained 26 wt. % of the product vinyl benzoate.

Experiment 13, Vinylation of Pivalic Acid

Preparation of Cu Co-Catalyst 2.13 g (15.8 mmol) of CuCl$_2$ and 4.4 g (15.8 mmol) of tetrabutylammonium chloride were mixed together as solid powders in a round bottom at room temperature. Then the flask was equipped with a magnetic stirrer, filled with nitrogen gas and moved into oil bath (preheated to 105° C.) for 1 h.

Preparation of the Reaction Phase 0.225 mg (1 mmol) of Pd(oAc)$_2$, 0.78 g (2.5 mmol) of tetrahexylammonium chloride together with 1.67 g the Cu co-catalyst described in this example were added to a high pressure reactor containing 46.4 g (453 mmol) of pivalic acid.

Vinylation reaction was carried out in typical way in the above examples.

Results

After 8 hours under said reaction conditions, a sample of the reaction liquid phase was analyzed by gas chromatography to determine the composition. The mixture contained 26.5 wt. % of the product vinyl pivalate.

Experiment 14, Vinylation of Adipic Acid

Preparation of the Reaction Phase 0.106 g (1 mmol) of Pd black, 0.79 g (2.5 mmol) of tetrahexylammonium chloride together with 2.6 g the Cu co-catalyst described in example 2 were added to a high pressure reactor containing 24.7 g (169 mmol) of adipic acid and 45.5 g of 1,4-dioxane.

Vinylation reaction was carried out in typical way in the above examples.

Results

After 21 hours under said reaction conditions, a sample of the reaction liquid phase was analyzed by gas chromatography to determine the composition. The mixture contained 6.8 wt. % of the product divinyl adipate.

Experiment 15, Vinylation of Crotonic Acid

Preparation of the Reaction Phase 0.106 g (1 mmol) of Pd black, 0.77 g (2.5 mmol) of tetrahexylammonium chloride together with 2.6 g the Cu co-catalyst described in example 2 were added to a high pressure reactor containing 56.9 g (661 mmol) of crotonic acid.

Vinylation reaction was carried out in typical way in the above examples.

Results

After 14 hours under said reaction conditions, a sample of the reaction liquid phase was analyzed by gas chromatography to determine the composition. The mixture contained 6.3 wt. % of the product vinyl crotonate.

Long Term Activity of the Catalyst:

The following experiment presented to demonstrate the long term activity of the Pd/Cu catalyst. Vinylation was carried out with lower amount of Pd catalyst (0.1 mmol) in order to demonstrate long term activity of the catalyst. Activity of the Pd/Cu catalyst as shown below in The FIGURE, displayed continuous activity for vinyl ester product more than 40 hours. This is only a representative example, the catalyst is capable to perform activities longer than this time periods.

Experiment 16, Long Term Activity of the Catalyst

Preparation of the Reaction Phase 1.06 g (0.1 mmol) of Pd black, 5.23 g of Cu co-catalyst described in the example 2, 5.399 g (32.339 mmol) of byphenyl (as internal standard) and 1.173 g (3 mmol) of tetrahexylammonium chloride were added to a high pressure reactor containing 60.0 g (348 mmol) of versatic acid 10.

Vinylation reaction was carried out in typical way in the above examples.

Results

TABLE 4

Vinylation of Neodecanoic acid with Pd catalyst, 0.1 mmol.

| Reaction time,. h | Vinyl ester, mmol |
|---|---|
| 0 | 0 |
| 2 | 0 |
| 4 | 7.3 |
| 6 | 23.3 |
| 10 | 45.1 |

TABLE 4-continued

Vinylation of Neodecanoic acid with Pd catalyst, 0.1 mmol.

| Reaction time, h | Vinyl ester, mmol |
|---|---|
| 14 | 61.4 |
| 20 | 82.1 |
| 27 | 98 |
| 34 | 119.2 |

Effect of Additives:

87 Additives such as molecular sieves, amines and quarternary ammonium slats displayed positive effect on the yield of VeoVa.

Experiment 17, Effect of Additives on the Yield of Vinyl Ester

Preparation of the Reaction Mixture 0.11 g (1 mmol) of Pd black, 2.6 g of Cu co-catalyst described in the example 2 and 5.4 g (35 mmol) of byphenyl (as internal standard) were added to a high pressure reactor containing 60.0 g (348 mmol) of versatic acid 10. In the last step, certain amount of an additive was introduced into the system. The vinylation reaction was carried out in typical way in the above examples.

Additive 1. 2.5 g of dry (120° C., 2 hours, vacuum) molecular sieves were added into the reactor.

Additive 2. 1.06 g (3.04 mmol) of trioctylamine.

Additive 3. 1.17 g (3 mmol) of tetrahexylammonium chloride

Results

Tables 5-8: Influence of additives on yield of VeoVa.

TABLE 5

| No additive | |
|---|---|
| Reaction time, h | Vinyl ester, mmol |
| 0 | 0.2 |
| 1 | 24.3 |
| 2 | 71.3 |
| 3 | 98.5 |
| 4 | 114.1 |
| 5 | 130.9 |
| 7 | 137.1 |
| 9 | 138.4 |
| 11 | 133.5 |

TABLE 6

| Additive = trioctylamine = $N_{888}$ | |
|---|---|
| Reaction time, h | Vinyl ester, mmol |
| 0 | 0 |
| 1 | 29.1 |
| 2 | 40.8 |
| 3 | 88.0 |
| 4 | 136.9 |
| 5 | 162.4 |
| 6 | 168.0 |

TABLE 7

| Additive = molecular sieves | |
|---|---|
| Reaction time, h | Vinyl ester, mmol |
| 0 | 0 |
| 0.9 | 73.0 |
| 1.7 | 120.6 |
| 2.5 | 205.1 |
| 4.5 | 160.7 |
| 6.5 | 214 |

TABLE 8

| Additive = tetrahexylammonium chloride = $N_{6666}Cl$ | |
|---|---|
| Reaction time, h | Vinyl ester, mmol |
| 0 | 0 |
| 1 | 29.1 |
| 2 | 40.8 |
| 3 | 88.0 |
| 4 | 136.9 |
| 5 | 162.4 |
| 6 | 185.0 |

What is claimed is:

1. A catalyst system comprising:
    a palladium (II) complex catalyst from a palladium precursor and organic salts; and
    a copper complex co-catalyst from a copper precursor and organic salts;
    wherein each of the palladium (II) complex catalyst and the copper complex co-catalyst are prepared ex-situ of the catalyst system,
    wherein the copper complex co-catalyst comprises from 2 to 400 molar equivalents to the palladium (II) complex catalyst molar equivalent, and
    wherein the catalyst system is free of copper salt precursors, and wherein each of the organic salts comprise an ionic organic salt, wherein the ionic organic salt comprises of cations based on quaternary or protonated alkyl, aryl or mixed alkyl-aryl ammonium, phosphonium, pyridinium, pyrrolium, piperidinium, pyrrolidiniumm, morpholinium, imidazolium, pyrazolium or a mixture thereof, and anions based on halogens, (halogenated)carboxylates, sulfates, alkylsulfates, alkylsulfonates, trifluoromethane sulfonate, tetrafluoroborate, hexafluorophosphate, phosphates, or a mixture thereof.

2. The catalyst system of claim 1, wherein the palladium precursor is selected from palladium (II) salts, wherein the palladium (II) salt comprises palladium (II) cation and an anion selected from $F^-$, $Cl^-$, $Br^-$, $I^-$, $R_nCOO^-$, $X_m$—$R_n$COO$^-$, acac$^-$, $X_k$-acac$^-$ $SO_4^{2-}$, $NO_3^{2-}$, $NO_2^-$, $CN^-$, $OCN^-$, $SH^-$, $R_nSO_4^-$, $X_m$—$R_nSO_4^-$, $NCS^-$, $R_nSO_3^-$, $X_m$—$R_nSO_3^-$ and combinations thereof; wherein $R_n$ is $C_n$ radical (n=1-20) selected from alkyl, aryl or cycloalkyl; wherein $X_m$—$R_n$, the $R_n$ is radical where m hydrogens are substituted by halogen X, m=1 to 2n+1; wherein acac is a acetylacetonate anion; $X_k$-acac is a halogenated form of acac, wherein k hydrogen atoms are substituted by halogen, k=1 to 6 or palladium (0) supported on a carrier material, palladium (0) colloid, palladium metal, palladium black or palladium complex, wherein the palladium (0) supported on carriers comprises either heterogeneous or soluble supports; wherein the heterogeneous supports are alumina, silica, alumina and silica, natural clays, metal oxides, metal halides, molecular sieves, anionic resin, carbons and carbon oxides, their allotropes, zeolites, insoluble polymers and combinations thereof and wherein the soluble supports material are soluble polymers, dendrimers and all listed materials from the heterogeneous supports group but in colloidal state.

3. The catalyst system of claim 1, wherein each of the organic salts are either ammonium salts or phosphonium salts or combinations thereof.

4. The catalyst system of claim 1, wherein the catalyst system consists essentially of:
  a palladium (II) complex catalyst from a palladium precursor and organic salts;
  a copper complex co-catalyst from a copper precursor and organic salts; and
  a carboxylic acid with a total of 3 to 20 carbon atoms, wherein each of the palladium (II) complex catalyst and the copper complex co-catalyst are prepared ex-situ of the catalyst system, wherein the copper complex co-catalyst comprises from 2 to 400 molar equivalents to the palladium (II) complex catalyst molar equivalent.

5. The catalyst system of claim 1, wherein the copper precursor is selected from Cu(II) salts or Cu(I) salts, wherein copper salts are Cu(II) or Cu(I) and anion selected from $F^-$, $Cl^-$, $Br^-$, $I^-$, $R_nCOO^-$, $X_m-R_nCOO^-$, $acac^-$, $SO_4^{2-}$, $NO_3^{2-}$, $NO_2^-$, $CN^-$, $OCN^-$, $SH^-$, $R_nSO_4^-$, $X_m-R_nSO_4^-$, $NCS^-$, $R_nSO_3^-$, $X_m-R_nSO_3^-$, $X_k$-acac and combinations thereof; wherein $R_n$ is $C_n$ radical (n=1-3) selected from alkyl, aryl or cycloalkyl; $X_m-R_n$, is $R_n$ radical where m hydrogens are substituted by halogen X, m=1 to 2n+1; acac is a acetylacetonate anion; $X_k$-acac is a halogenated form of acac, where k hydrogen atoms are substituted by halogen, k=1 to 6.

6. The catalyst system of claim 3, wherein each of the organic salts are tetra butyl ammonium chloride, tetra hexyl ammonium chloride, trihexyltetradecyl phosphonium chloride or combinations thereof.

7. The catalyst system of claim 1,
  wherein the catalyst system is disposed in a carboxylic acid with a total of 3 to 20 carbon atoms as a substrate to form a reaction liquid phase,
  wherein the carboxylic acid comprises linear alkyl, or a branched alkyl, or aryl, or alkyl-aryl, or alkenyl, or alkenyl-aryl,
  wherein the carboxylic acid is mono or multi-functional,
  wherein the carboxylic acid contains heteroatoms in or along the carbon atom backbone and the heteroatoms are selected from the group consisting of halogens, N, O, P, and S and combinations thereof,
  and combination thereof.

8. The catalyst system of claim 1, wherein the carboxylic acid comprises neodecanoic acid, lauric acid, 2-ethylhexanoic acid, benzoic acid, and combinations thereof.

9. The catalyst system of claim 1, wherein the catalyst system is organic solvent-free.

* * * * *